(12) United States Patent
Knauer et al.

(10) Patent No.: US 7,731,487 B2
(45) Date of Patent: Jun. 8, 2010

(54) MOLD FOR FORMING A HEARING PROTECTIVE DEVICE

(75) Inventors: Richard Knauer, Indianapolis, IN (US); Alan R. Seville, Indianapolis, IN (US); Robert N. Falco, Indianapolis, IN (US); James Hall, Lincoln, RI (US); Lori S. Hall, legal representative, Lincoln, RI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/357,768

(22) Filed: Feb. 17, 2006

(65) Prior Publication Data

US 2006/0141083 A1 Jun. 29, 2006

Related U.S. Application Data

(62) Division of application No. 09/990,654, filed on Nov. 21, 2001, now abandoned.

(60) Provisional application No. 60/253,433, filed on Nov. 28, 2000.

(51) Int. Cl.
*B29C 44/12* (2006.01)
(52) U.S. Cl. .................. 425/4 R; 425/110; 425/127; 425/812; 425/817 R
(58) Field of Classification Search ............. 425/4 R, 425/110, 127, 129.1, 812, 817 R
See application file for complete search history.

(56) References Cited

U.S. PATENT DOCUMENTS

| 2,538,339 | A | | 1/1951 | Thomas | 128/864 |
|---|---|---|---|---|---|
| 2,790,205 | A | * | 4/1957 | Parker | 425/52 |
| 2,804,072 | A | | 8/1957 | Genzer | 128/864 |
| 3,148,430 | A | * | 9/1964 | Hanner | 425/408 |
| 3,800,791 | A | | 4/1974 | Visor | 128/864 |
| RE29,487 | E | | 12/1977 | Gardner, Jr. | 128/864 |
| 4,412,962 | A | * | 11/1983 | Bessette et al. | 264/46.4 |
| 4,434,794 | A | | 3/1984 | Leight | 128/867 |
| 4,443,173 | A | * | 4/1984 | Mansberger, II | 425/126.1 |
| 4,461,290 | A | | 7/1984 | Gardner, Jr. et al. | 128/866 |
| 4,666,323 | A | * | 5/1987 | Kessler | 425/805 |
| 4,671,265 | A | | 6/1987 | Andersson | 128/866 |
| 4,784,366 | A | * | 11/1988 | Muller | 249/91 |
| 4,795,331 | A | * | 1/1989 | Cain et al. | 425/28.1 |
| 5,044,463 | A | | 9/1991 | Carr | 128/864 |
| 5,071,331 | A | | 12/1991 | Falco | 425/4 R |
| 5,087,188 | A | * | 2/1992 | Staver | 425/116 |

(Continued)

FOREIGN PATENT DOCUMENTS

DE    1 566 341    7/1970

(Continued)

OTHER PUBLICATIONS

International Search Report; PCT/US01/44236; May 10, 2002.

*Primary Examiner*—Robert B Davis
*Assistant Examiner*—Joseph Leyson
(74) *Attorney, Agent, or Firm*—Karl G. Hanson (57) ABSTRACT

A mold for forming a foam earplug including a lower mold portion including a lower cavity; and an upper mold portion including an upper cavity and a means for venting a gas during a rising of the foam, wherein the lower and upper mold portions are engageable so as to communicably engage the lower and upper cavities.

6 Claims, 12 Drawing Sheets

U.S. PATENT DOCUMENTS

| | | | |
|---|---|---|---|
| 5,188,123 A | 2/1993 | Gardner, Jr. | 128/864 |
| 5,203,352 A | 4/1993 | Gardner, Jr. | 128/864 |
| 5,344,601 A | 9/1994 | Newton | 264/255 |
| 5,792,998 A | 8/1998 | Gardner, Jr. et al. | 181/130 |
| 5,799,658 A | 9/1998 | Falco | 128/864 |
| 5,997,783 A * | 12/1999 | Hunter et al. | 264/51 |
| 6,105,715 A | 8/2000 | Knauer | 181/135 |
| 6,364,052 B1 | 4/2002 | McLean | 181/135 |
| 6,427,800 B1 | 8/2002 | Hiselius et al. | 181/135 |
| 2003/0029458 A1 | 2/2003 | Tiemens | 128/864 |
| 2003/0029459 A1 | 2/2003 | Tiemens | 128/864 |
| 2003/0029460 A1 | 2/2003 | Tiemens | 128/864 |

FOREIGN PATENT DOCUMENTS

| | | |
|---|---|---|
| FR | 2 230 336 | 12/1974 |
| GB | 2 100 606 | 1/1983 |
| WO | WO 91 07914 | 6/1991 |

* cited by examiner

MOLD FOR FORMING A HEARING PROTECTIVE DEVICE

CROSS REFERENCE TO RELATED APPLICATIONS

This application is a Divisional of U.S. patent application Ser. No. 09/990,654 filed on Nov. 21, 2001, now abandoned, which claims priority to U.S. Provisional Patent Application Ser. No. 60/253,433 filed on Nov. 28, 2000, both of which said applications are herein incorporated by reference in their entirety.

BACKGROUND

The present invention relates generally to hearing protective devices, and more particularly to hearing protective devices including a semi-rigid component.

The use of hearing protective and noise attenuating devices are well known, and various types of devices are available for this purpose. Such devices include, but are not limited to, earplugs and semi-aural devices. Foam components are well known for use with these devices, providing both sound attenuation and enhanced comfort for the wearer.

Earplugs are generally preferred for continuous use over longer periods of time. Foam earplugs composed of resilient polymer foam materials such as foam rubber or polyurethane are well known in the art. Slow recovery foam earplugs, such as those disclosed in U.S. Reissue. No. 29,487 to Gardner, Jr., are not only comfortable, but have also been shown to deliver high in-field noise protection at all frequencies. U.S. Pat. No. 5,203,352 to Gardner, Jr. also discloses a hearing protective earplug comprising a polymeric foam.

A hearing protective device may further include a cord that is attached to a pair of earplugs and extends therebetween. Conventional cords are commonly designed so that the cord may be permanently attached to the earplugs and more specifically, each end of the cord may be permanently attached to stem portions of the respective earplugs.

A typical semi-aural hearing protector assembly generally includes a resilient U-shaped band with holders at opposite ends, and a pair of inwardly directed ear protectors ("pods") that are detachably mounted to the holders. Semi-aural hearing protectors that enter the ear canal offer hearing protection but are somewhat less comfortable than those that simply cap the ear. U.S. Pat. No. 4,461,290 to Gardner, Jr. et al. discloses a semi-aural device incorporating a foam component. U.S. Pat. No. 4,671,265 to Anderson also discloses a semi-aural device.

With respect to these devices, the sound-attenuating (acoustical) component has been made both of flexible, rubber-like materials, and of foam. For earplugs and semi-aural devices, the rubber-like materials are advantageous because they allow the earplug or device to be directly inserted into the wearer's ear. However, such earplugs and devices typically become uncomfortable over long periods of use. Foam earplugs provide enhanced comfort, but may require rolling down before insertion.

Figure 1:
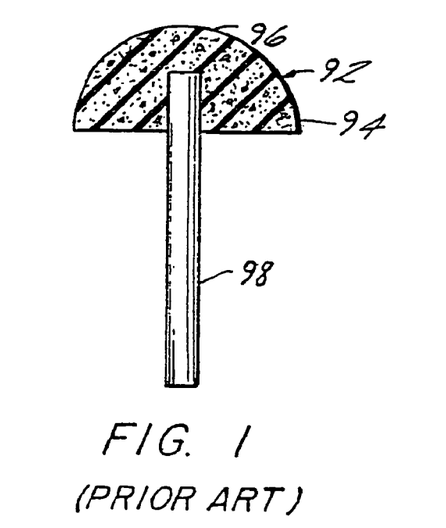
FIG. 1 is a conventional earplug.

A foam earplug with a stem can provide both the ease of insertion of rubber-like earplugs and the comfort of foam earplugs. A number of patents disclose earplugs having tips or flanges with a relatively stiff stem used to insert and remove the earplug. One earplug, shown in Prior Art FIG. 1, is described in U.S. Pat. No. 5,188,123 to Gardner, herein incorporated by reference. This earplug includes a circular or ovoid resilient polymeric foam body having a rounded nose end. An elongated stem is axially embedded in the foam body and extends rearward and axially therefrom. The earplug may be used in a push-in or roll-down insertion mode.

While suitable for certain purposes, this prior art earplug requires an additional manufacturing step over conventional plugs to secure the stem in the foam body. Also, the material of the foam body is prone to peel from the insert. In addition, inclusion of a hard stem in the earplug could be a hazard for the user, the general concern being that potential injury could result should the hearing protector become impacted. On the other hand, if the stem is too soft, it tends to buckle upon insertion, limiting the fit of the earplug and reducing the potential usefulness of the stem.

Another attempted solution to the above-discussed deficiencies in the art is the use of a porous component as a stem as disclosed in U.S. Pat. No. 5,799,658 to Falco. Therein, individual porous stems are mechanically bonded to the foam during manufacture by controlled penetration of the foam by the porous component stem. However, the individual porous stems are relatively expensive and somewhat difficult to manufacture.

Accordingly, there remains a need for a stemmed foam earplug that is effective in providing hearing protection, yet convenient and comfortable to use, and has a more efficient and lower cost method of manufacture.

SUMMARY

The above discussed and other problems and deficiencies of the prior art are overcome or alleviated by the hearing protective device and method of manufacture of the invention.

In a preferred embodiment, an earplug comprises a foam and at least one component that is nestable with and bondable with the foam. The component is disposed at least partially within a foam insertable portion and at least partially within a foam handle portion.

In the preferred method of the present invention, the component is initially disposed in a mold. A foam or foamable mixture is introduced into the mold causing the foam to rise and surround the component. The component is nestable with and bondable with the foam. Also the component is at least partially within a foam insertable portion and at least partially within a foam handle portion.

In another preferred embodiment, a venting portion is provided in the mold. In still another preferred embodiment, a venting portion is provided on the component. The venting portions allow gas to escape the mold during rising of the foam. Further, the venting portions retain the foam within the mold during rising, thus preventing spillage of the foam outside the mold. Also, an amount of the foam is permitted to cure in the venting portion to effectively seal off the mold thus maintaining a pressure within in the mold desirable for curing of the foam therein.

The above discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES.

DESCRIPTION OF THE PREFERRED EMBODIMENT

The device and method of manufacture of the invention comprises a foam and at least one component nestable with and bondable with the foam and a method of forming the same.

Figure 2:
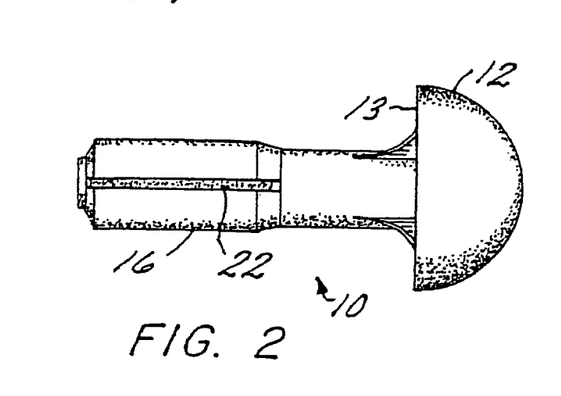
FIG. 2 is an elevational view of an earplug, according to one embodiment of the invention.
Figure 3:
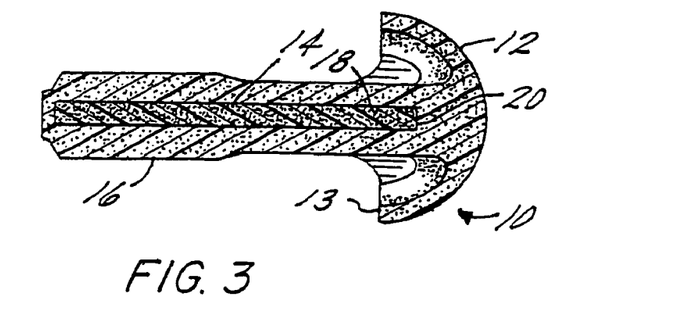
FIG. 3 is a cross-sectional view of the earplug of FIG. 2.

Referring now to FIGS. 2 and 3, in a preferred embodiment, a uniform foam earplug 10 comprises a foam insertable portion 12 and a foam handle portion 16. The foam substantially surrounds, encapsulates, or is nestable with and bondable with a component 14 having an embedded portion 18 with a tip 20. The embedded portion refers herein to that part of the component that is at least partially located within, and is bonded to, the foam insertable portion 12 and the foam handle portion 16. The foam handle portion 16 has a smaller diameter than the foam insertable portion 12. A depression 22, illustrated in FIG. 2 as a longitudinal groove, may extend within the foam handle portion 16 at least partially along the component 14. As is preferred, the earplug has a flange configuration 13. Alternate depressions (or a lack of depressions) and alternative earplug configurations are of course contemplated by the invention.

Figure 4:
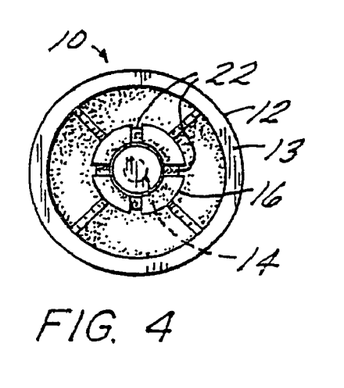
FIG. 4 is an end view of the earplug of FIG. 2.

Referring now to FIG. 4, an end view of the exemplary earplug 10 is illustrated. The component 14 is disposed within the foam handle portion 16. As is illustrated by this embodiment, depressions 22 (four longitudinal grooves are shown) extend at least partially through the foam handle portion 16 and at least partially along a portion of the component 14.

Figure 5:
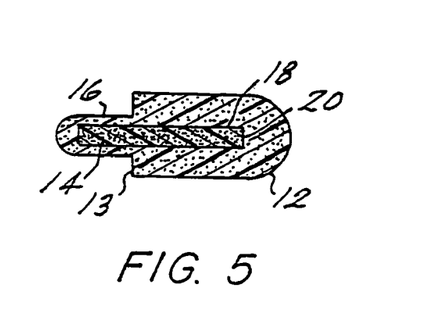
FIG. 5 is a cross-sectional view of the earplug of FIG. 2 in another embodiment.
Figure 6:
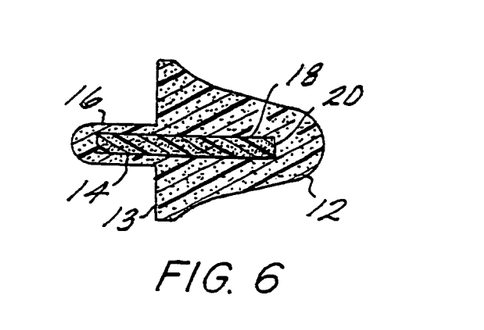
FIG. 6 is a cross-sectional view of the earplug of FIG. 2 in another embodiment.
Figure 7:
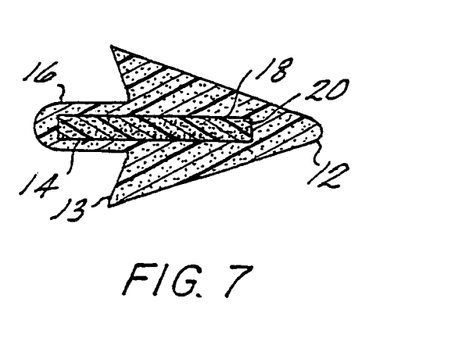
FIG. 7 is a cross-sectional view of the earplug of FIG. 2 in another embodiment.
Figure 8:
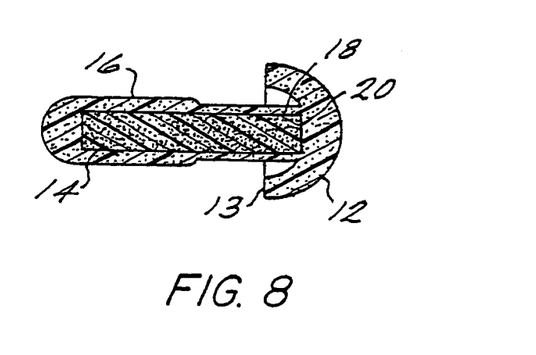
FIG. 8 is a cross-sectional view of the earplug of FIG. 2 in another embodiment.

Referring now to FIGS. 5-8, the preferred embodiments of the present invention are shown. Each figure illustrates a foam insertable portion 12, a flange 13, a component 14, a foam handle portion 16, an embedded portion 18, and a tip 20. FIG. 5 illustrates a bullet-shaped earplug. FIG. 6 illustrates a bell-shaped earplug. FIG. 7 illustrates a cone-shaped earplug. FIG. 8 illustrates a mushroom-shaped earplug.

Figure 9:
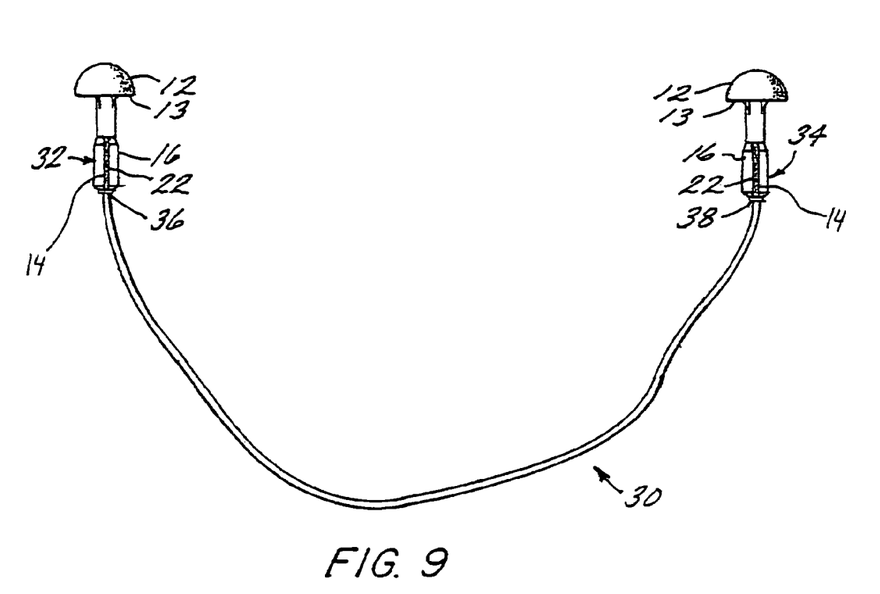
FIG. 9 is a perspective view of a set of corded earplugs.

The foam handle portions of two earplugs may be each attached to the end of a cord, an under-the-chin device, or a headband by bonding methods known in the art. Turning now to FIG. 9, a preferred embodiment includes respective earplugs 32, 34 that are each attached to respective ends 36, 38 of a cord of a device, shown generally at 30. FIG. 9 illustrates the foam insertable portion 12, the flange 13, the foam handle portion 16, and the longitudinal groove 22. The figure also illustrates the attachment of the cord ends 36, 38 to a passageway within the component 14 (e.g. a hollow component) of the earplugs.

Other means of cord attachment are contemplated, including attachment to at least one depression 22, to an exterior of the foam handle portion 16, and to an end of the component 14 (e.g., a solid component), among others.

The attachment of the earplugs 32, 34 to cord ends 36, 38 may occur by any known method in the art, but is preferably performed thermally, ultrasonically, or by crimping. Where the earplug and the cord materials are dissimilar, or where such materials do not form a strong bond under thermal or ultrasonic conditions, adhesives may additionally or alternatively be used.

Figure 10:
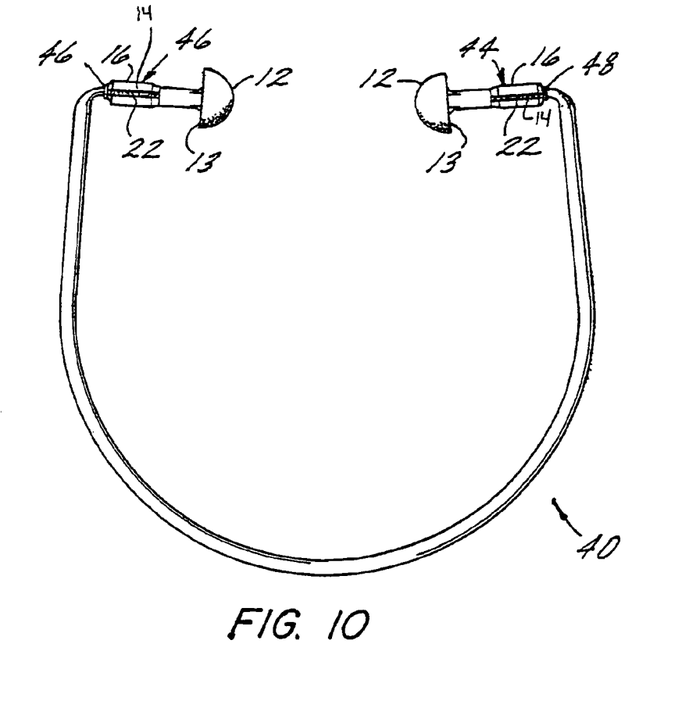
FIG. 10 is a perspective view of foam components and a semi-rigid headband for a semi-aural device.

Referring now to FIG. 10, a semi-aural device 40 is shown including earplugs 42, 44 attached to an under the chin device or headband component 45. The earplugs 42, 44 are each at least partially attached to respective ends 46, 48 of the headband 45. FIG. 10 illustrates the attachment of the earplugs 42, 44 to the headband ends 46, 48. The figure also illustrates the foam insertable portion 12, the flange 13, the component 14, the foam handle portion 16, and a longitudinal groove 22. The earplugs may attach to the headband by any method known in the art. The attachment method provides for the ability to remove the earplugs for replacement or cleaning.

Referring again to FIGS. 2-4, preferably, the component 14 is used as a stem of the earplug 10. As such, the component 14 should be rigid enough to aid insertion into the wearerls ear, yet soft and pliable enough to be comfortable and safe for the wearer. The semi-rigid component 14 should be selected of a material that is compatible with the foam of the insertable portion 12 and creates a bond between the component and the foam. Thus, the material is preferably a plastic material, but other embodiments may include paper, dense paper, rubber, foam, stiff foam, porous foam, relatively or semi-stiff foam, cardboard, or combinations thereof. The preferred component 14 can have disposed within at least one passage, such that the component 14 is hollow. Other passages (i.e. voids or relief cuts) are also contemplated for the component. The component 14 may also be of a solid or dense construction, and may include at least one passage. The component may also have disposed therein at least one indentation, dip or dimple.

Additionally, the component 14 may be of a different color than the foam of the earplug 10, such that the color of the component 14 is visible through the one or more depressions 22 that may be formed in the handle portion 16, thus clearly distinguishing the handle portion 16 of the earplug 10 for ease in inserting, removing, and otherwise identifying the earplug 10. The depression 22 may be in the form of longitudinal grooves, relief cuts, letters or designs, or the like. An earplug 10 with a hollow component 14 may be manufactured such that components of a receiver, or other communication devices, may be attached to the earplug for communication purposes.

Suitable foams for use with the earplug 10 include those foams known in the art to be appropriate for use with foam earplugs or other foam components for hearing protective devices. For example, such foams may include soft, pliable self-rising foams with instant recovery. Suitable foams may also include polyurethane or acrylic blend foams with slow recovery. Other foams include PVC, silicone, and nitrile, among others. A suitable foam is described in U.S. Pat. No. 5,792,998 to Gardner, Jr. et al., herein incorporated by reference. The earplug described therein is comprised of a dynamically stiff foam material having a low static stiffness, and a high dynamic stiffness. Another suitable foam is described in U.S. Pat. No. 4,158,087 to Wood, herein incorporated by reference.

In a method of manufacturing the earplug 10 of FIGS. 1-8, the component 14 is disposed, suspended, or placed into a cavity of an earplug mold. A foam or a foamable mixture is introduced into the mold, and caused to rise. Rising may be accomplished by any suitable means, for example by using a self-rising foam. As the foam rises, it at least partially surrounds, encapsulates, or is nestable with and bondable with, or bonds to, the component. Molding may be performed with any suitable molding process and device such as is known in the art.

Figures 11, 12:
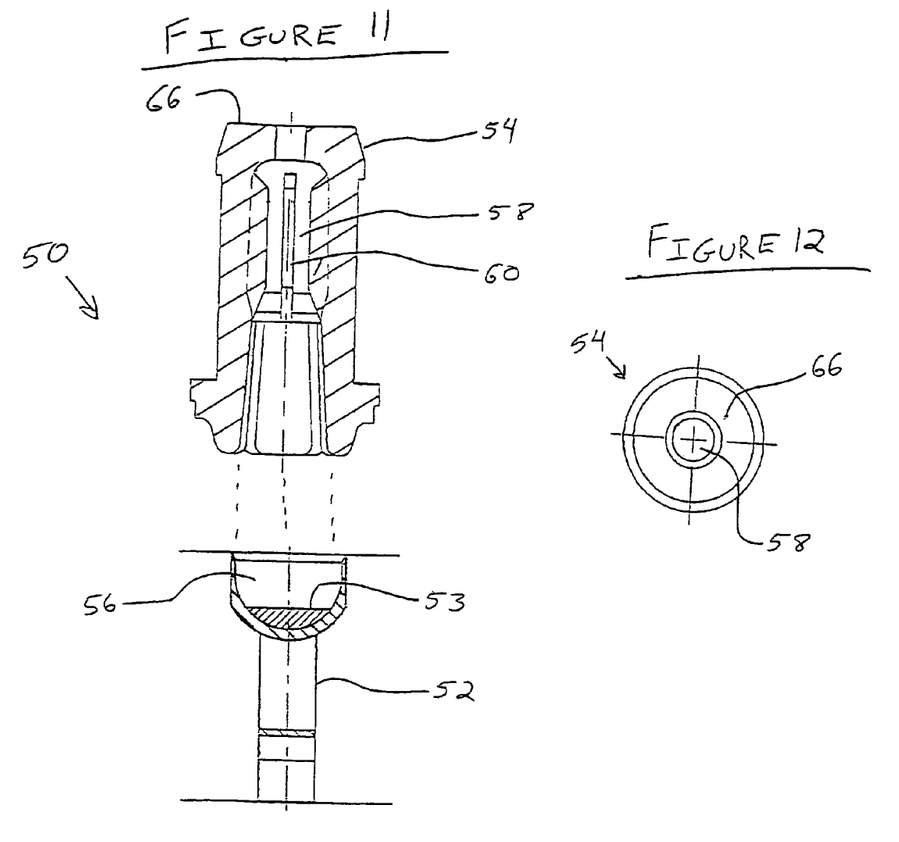
FIG. 11 is a cross-sectional view of one embodiment of a mold for forming the earplug of FIG. 2.
FIG. 12 is a top view of the mold of FIG. 11.

An earplug mold 50, as shown in FIG. 11, includes a mold lower portion 52 and a mold upper portion 54.

The mold lower portion 52 is made of a rigid, non-porous material, for example, a polymeric material such as polypropylene or high-density polyethylene. Also, the mold lower portion 52 may be made of a metal such as aluminum. The mold lower portion 52 includes a lower cavity 56 for receiving and shaping a foam or foamable mixture 53 to form the foam insertable portion 12 of the earplug 10.

The mold upper portion 54 of the earplug mold 50 is made of a flexible material, for example, thermoplastic rubber, thermoset rubber, etc., and includes an upper cavity 58 for receiving and retaining the component 14 during manufacture of the earplug 10 and for receiving and shaping the rising foam 53, as discussed herein. In one embodiment, the component 14 is retained in the mold upper portion 54 by ribs 60 disposed in the cavity 58. In one embodiment, the ribs 60 include four flanges which project inwardly into the cavity 58 and traverse the cavity 58 in a longitudinal direction thereof.

Figure 13A:
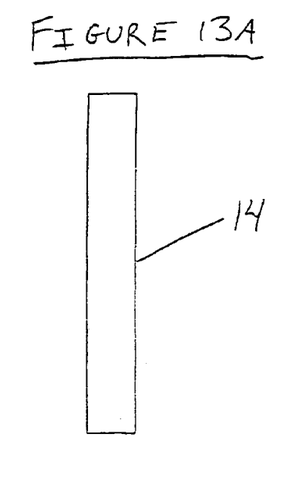
FIG. 13A is an elevational view of one embodiment of a component stem of the earplug of FIG. 2.

To manufacture the earplug 10, the foam 53 is disposed in the mold lower cavity 56. The component 14, particularly shown in FIG. 13A, is inserted in the upper portion 54 such that the component 14 contacts the ribs 60 and is thus retained within the cavity 58. The mold upper portion 54 is positioned proximate the mold lower portion. The cavity 56 communicably engages the cavity 58. The foam 53 is allowed to rise from the cavity 56 into the cavity 58 and to encapsulate the component A bond is formed between the foam 53 and the encapsulated component 14. The foam is shaped by the lower and upper mold portions 52, 54, the foam 53 is allowed to cure, and then the foam 53 and component 14 are ejected from the mold 50 as the earplug 10.

Figure 13B:
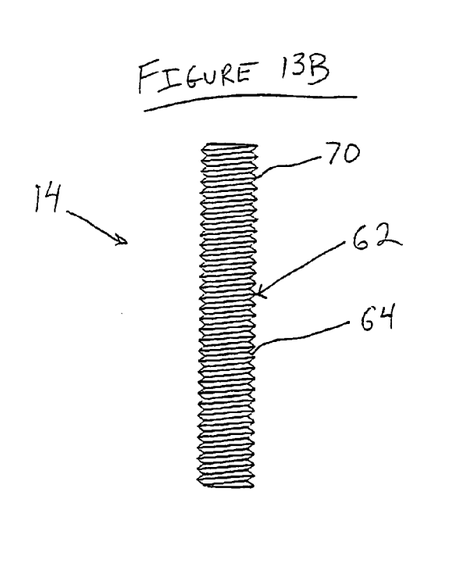
FIG. 13B is an elevational view of another embodiment of the component stem of FIG. 13A.
Figure 13C:
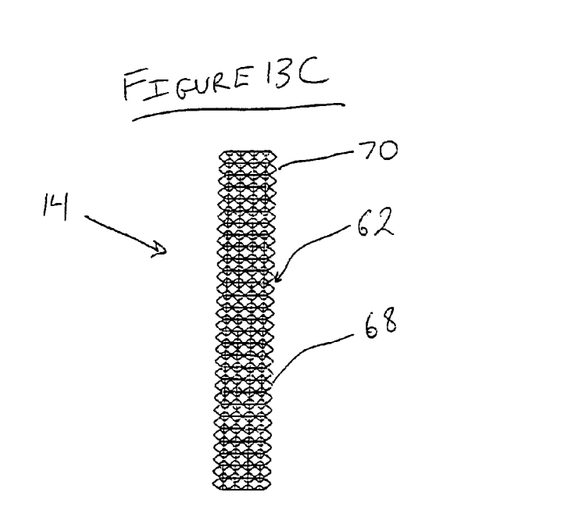
FIG. 13C is an elevational view of another embodiment of the component stem of FIG. 13A.

In another embodiment, the component 14 includes component venting means 62, as shown in FIGS. 13B and 13C, to allow for a gas to escape from the mold cavities 56, 58 during manufacture of the earplug 10. Specifically, the component venting means 62 allows for gas to escape the cavities during the foaming process, that is, during rising and rising of the foam within the mold 50. The vented gas includes air originally present within the mold prior to the foaming process and any gas that may be evolved during the process.

The component venting means 62, in one embodiment, includes screw threads 64 disposed helically about the component 14. The screw threads 64 contact the mold upper portion 54 in the upper cavity 58 at least at a top end 66 of the mold upper portion 54. The contact of the screw threads 64 with the mold upper portion 54 forms vent passages there between which allow passage of gas during the foaming process. That is, vent passages are delimited by the screw threads 64 and a surface of the top end 66 of the upper mold portion 54 forming the upper mold cavity 58. The component 14 having screw threads 64 extends from the upper cavity 58 such that the vent passages traverse from the upper cavity 58 to an exterior of the of the mold upper portion 54. Thus, the vent passages allow gas to travel from the cavities 56, 58 to the exterior of the mold 50 during the foaming process. More specifically, as the foaming process commences, the foam begins to rise and occupy an increased volume of the mold cavities 56, 58, thus increasing the pressure within the cavities 56, 58. Due to this increased pressure, air residing within the mold cavities 56, 58 prior to commencement of the foaming process is forced out of the mold cavities 56, 58 through the vent passageways to an exterior of the mold 50.

The component venting means 62, in another embodiment, includes knurls 68, as shown in FIG. 13C. The knurls 68 are protrusions formed along the length of the component 14 which extend radially therefrom. When the component 14 having knurls 68 is inserted in the mold upper portion 54, the knurls 68 contact the mold upper portion 54 to form vent passageways therebetween. That is, the vent passageways are delimited by the knurls 68 and the surface of the top end 66 of the upper mold portion 54 forming the upper mold cavity 58. The vent passageways permit gas to travel from the cavities 56, 68 to the exterior of the mold 50 during the foaming process similarly as discussed above with reference to the screw threads 64.

The screw threads 64 and the knurls 68, in one embodiment, are formed along the length of the component 14. In another embodiment, the screw threads 64 and the knurls 68 are formed only at a top end 70 of the component 14. In still another embodiment, the screw threads 64 and knurls 68 are formed only at a confined portion located somewhere between respective ends of the component 14, for example, at a midpoint between the respective ends. The top end 70 of the component 14 contacts the top end 66 of the mold upper portion 54 when the component 14 is inserted in the mold upper portion 54 during the manufacture of the earplug 10.

Size and spacing of the screw threads 64 and the knurls 68 are predetermined to allow a certain volume of gas to pass through the vent passageways when a certain pressure accumulates in the cavities 56, 58 during the foaming process. Further, the screw threads 64 and the knurls 68 are designed to prevent passage of the rising foam 53 from the cavities 56, 58 to the exterior of the mold thus preserving the integrity of the mold 50 and reducing waste during the molding process.

Additionally, the screw threads 64 and the knurls 68 allow a certain volume of the rising foam 53 to enter the vent passageways and cure therein effectively sealing off the mold cavities 56, 58 from the exterior of the mold 50. That is, after the excess air within the mold cavities 56, 58 is vented, the rising foam 53 is permitted to fill the vent passageways and to cure therein. More specifically, the rising foam is directed through the vent passageways which act in this instance essentially as a tortuous path to shear a portion of the foam causing the foam to collapse and/or densify and cure therein to seal off the vent passageways. This sealing effect serves to maintain a pressure within the mold cavities 56, 58 optimal for curing of the foam and, hence, or formation of the earplug 10.

As a result of the densification of the foam at the vent passageways, the resulting earplug 10, as shown in FIGS. 2-4, includes foam formed at the screw threads 62 or the knurls 64. That is, foam which cures in the vent passageways to form the effective seal of the mold 50 is removed from the mold 50 as a portion of the earplug 10. The foam at the screw threads 62 or knurls 64 has a greater hardness and a higher density than foam formed at the insertable and handle portions 12 and 16, respectively.

Figure 14A:
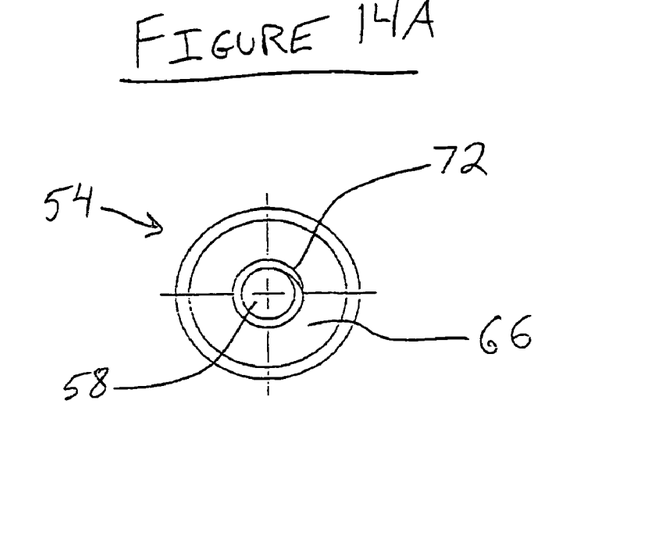
FIGS. 14A-14B are various views of another embodiment of a mold upper portion of FIG. 11.
Figure 14B:
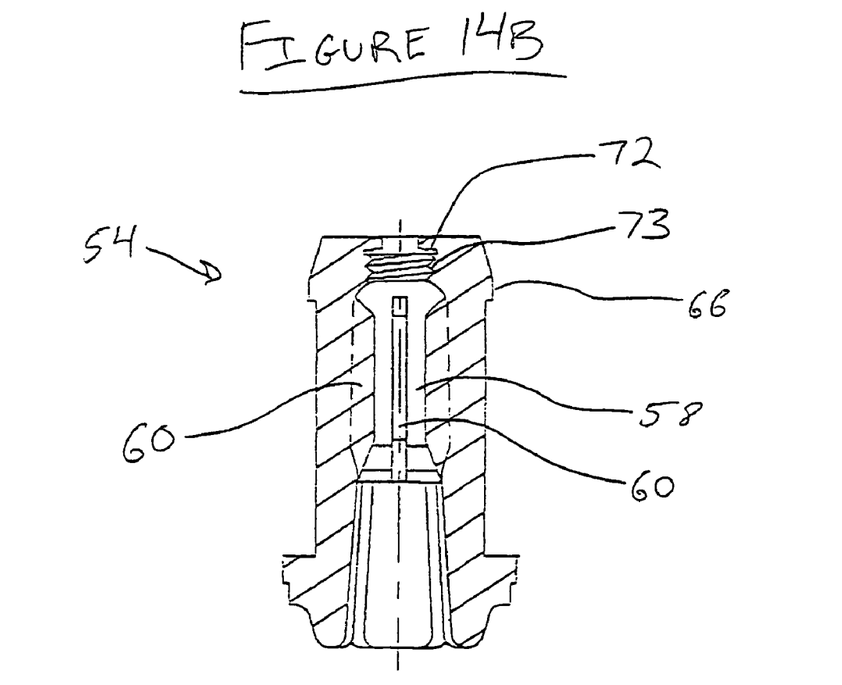

In another embodiment, shown in FIGS. 14A and 14B, the mold upper portion 54 includes a screw vent portion 72 formed at the top end 66. The screw vent portion 72 includes screw threads 73 formed helically on the mold upper portion 54 along a longitudinal axis of the upper cavity 58.

During manufacture of the earplug 10, the component 14 of FIG. 13A is inserted in the upper mold portion 54 of FIG. 14B and retained therein by the ribs 60. The component 14 contacts the screw threads 73 of the screw vent portion 72 to form helical vent passages extending from the upper cavity 58 to the exterior of the mold upper portion 54. During the foaming process, gas, particularly air originally disposed within the cavities, travels from the upper cavity 58 through the vent passages to the exterior of the mold upper portion 54, similar to that described above with reference to the screw threads 64 formed on the component 14 shown in FIG. 13B.

Figure 15A:
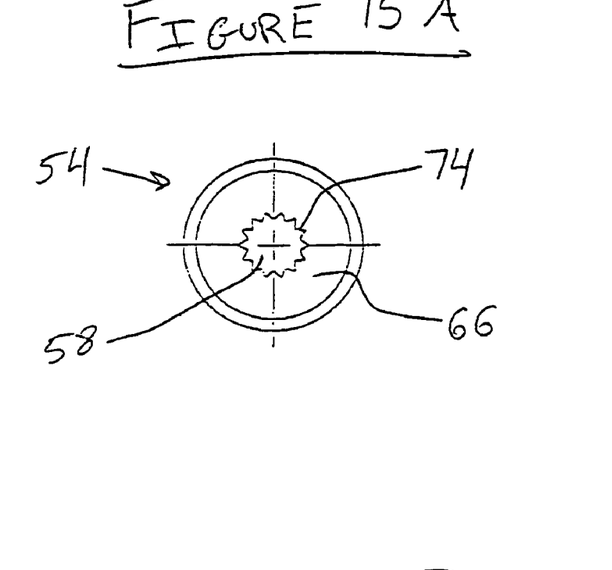
FIGS. 15A-15B are various views of another embodiment of the mold upper portion of FIG. 11.
Figure 15B:
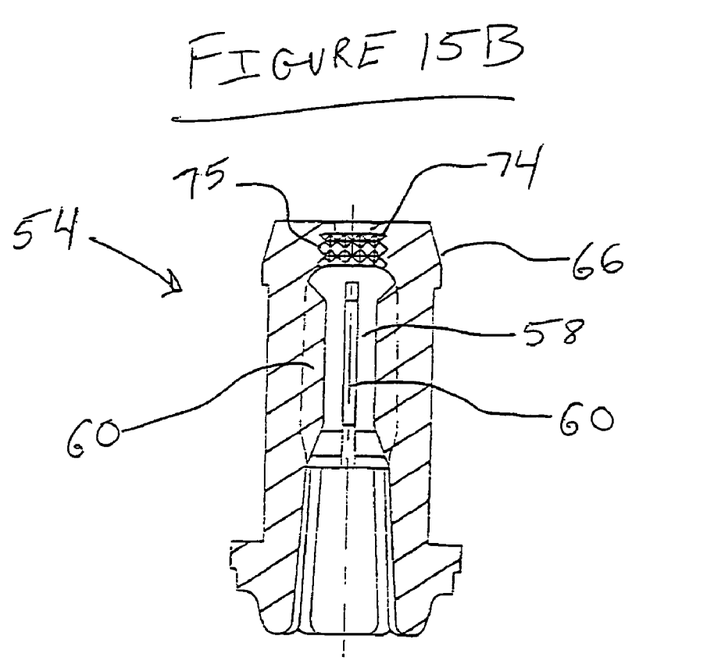

In another embodiment, shown in FIGS. 15A and 15B, the mold upper portion 54 includes a knurled vent portion 74 formed at the top end 66. The knurled vent portion 74 includes knurls 75 protruding into the mold upper cavity 58. During manufacture of the earplug 10 using this embodiment of the mold upper portion 54, the component 14 of FIG. 13A is inserted in the cavity 58 and retained therein by the ribs 60 such the component 14 contacts the knurls thus forming vent passageways therebetween. During the foaming process, gas, particularly air originally disposed within the cavities, travels from the upper cavity 58 through the vent passages to the exterior of the mold upper portion, similar to that described above with reference to the knurls 68 formed on the component 14 shown in FIG. 13C.

Figure 16A:
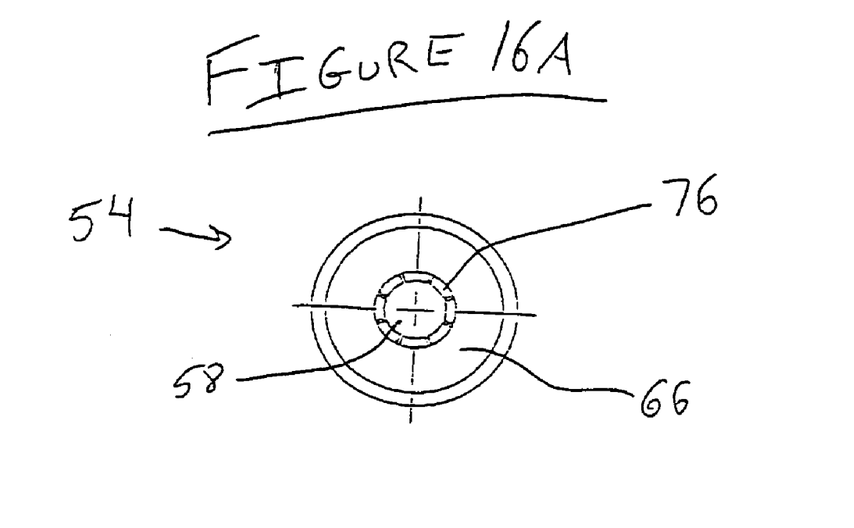
FIGS. 16A-16B are various views of another embodiment of the mold upper portion of FIG. 11.
Figure 16B:
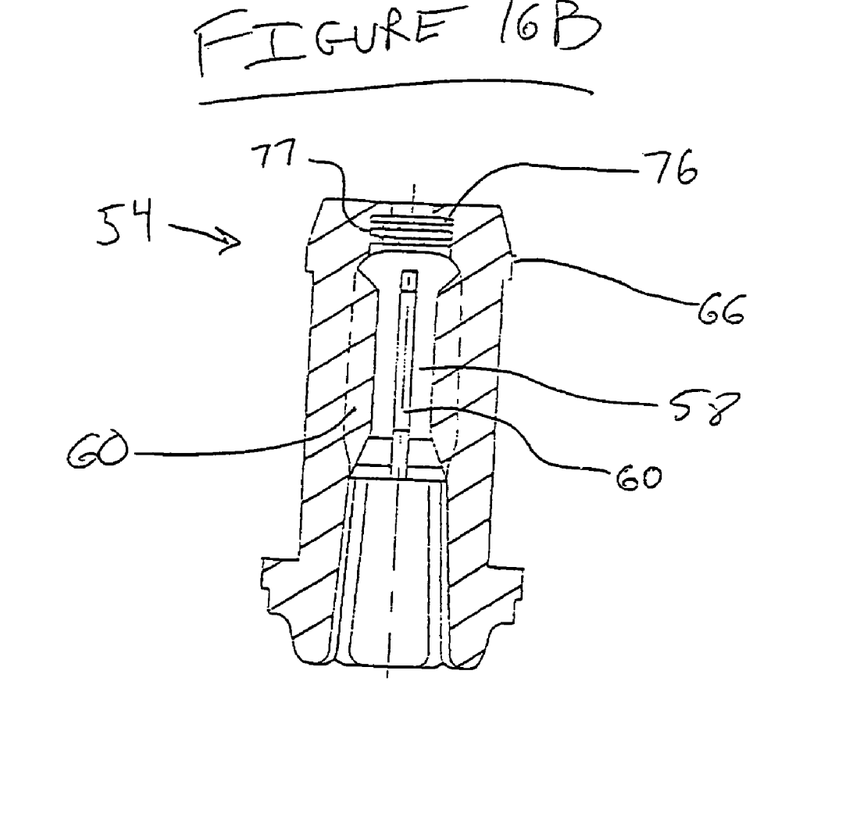

In another embodiment, shown in FIGS. 16A and 16B, the mold upper portion 54 includes a flange vent portion 76 formed at the top end 66. The flange vent portion 76 includes annular flanges 77 formed on the mold upper portion 54 about a longitudinal axis thereof and projecting into the upper cavity 58. The flanges 77 include at least one space formed respectively therein. More preferably, the flanges include a plurality of spaces formed periodically across the annular distance of the flanges.

During manufacture of the earplug 10 using the mold upper portion 54 having the flange vent portion 76, the component 14 of FIG. 13A is inserted in the cavity 58 and retained therein by the ribs 60 such the component 14 contacts the flanges. Vent passageways are formed between the component 14 and the mold upper portion 54 by communication of the spaces in the flanges 77. Accordingly, during the foaming process, gas, particularly air originally disposed within the cavities, is permitted to travel from the upper cavity 58 through the vent passages formed by the communication of the annular tabs 77 and the upper mold portion 54 to the exterior of the mold upper portion, thus allowing optimal production of the earplug 10.

The upper mold portion 54 including at least one of the screw vent portion 72, knurl vent portion 74, and flange vent portion 76, as mentioned, allows gas to travel from the mold cavities 56, 58 to the exterior of the mold 50. Specifically, during the foaming process, the foam 53 rises within the cavities 56, 58 thus increasing the pressure therein. This increased pressure forces air originally present within the cavities 56, 58 to travel through the vent passages to the exterior of the mold 50. This venting allows proper rising and formation of the foam 53.

Additionally, the upper mold portion 54 including at least one of the screw vent portion 72, knurl vent portion 74, and flange vent portion 76, prevents overflow of the rising foam material 53 to the exterior of the mold 50 thus preserving the integrity of the mold 50 and reducing waste associated with the molding process.

Further, the upper mold portion 54 including at least one of the screw vent portion 72, knurl vent portion 74, and flange vent portion 76, allows a certain volume of the rising foam 53 to enter the vent passageways and cure therein effectively sealing off the mold cavities 56, 58 from the exterior of the mold 50. That is, after the excess air within the mold cavities 56, 58 is vented, the rising foam 53 is permitted to fill the vent passageways and to cure therein. This sealing effect serves to maintain a pressure within the mold cavities 56, 58 which is optimal for curing of the foam and, hence, for formation of the earplug 10.

FIGS. 17A-17H show a method of manufacturing the earplug 10 using the mold upper portion 54 including the screw vent portion 72.

Figure 17A:
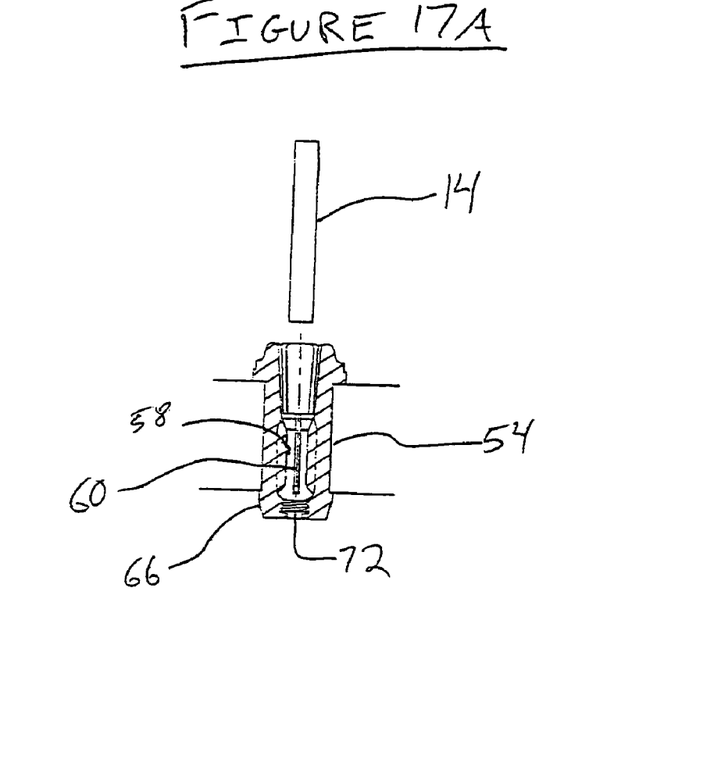
FIGS. 17A-17H show one embodiment of a method for manufacturing the earplug of FIG. 2.
Figure 17B:
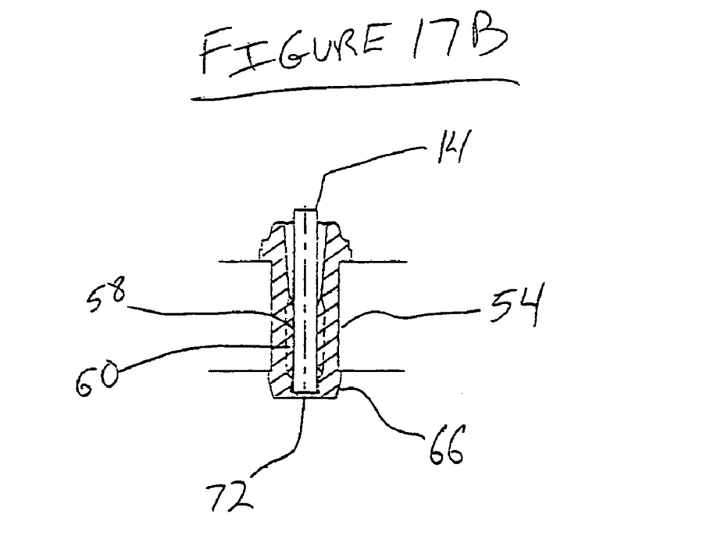
Figure 17C:
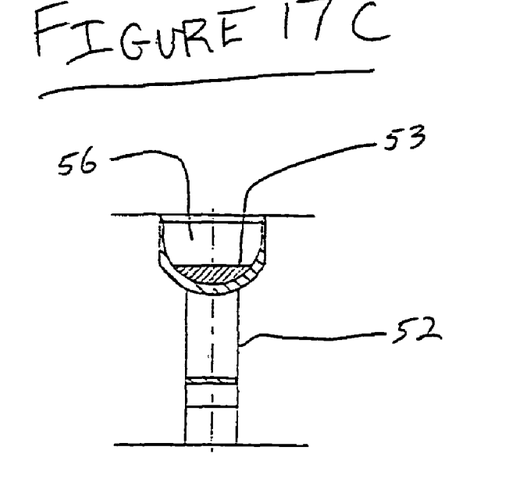
Figure 17D:
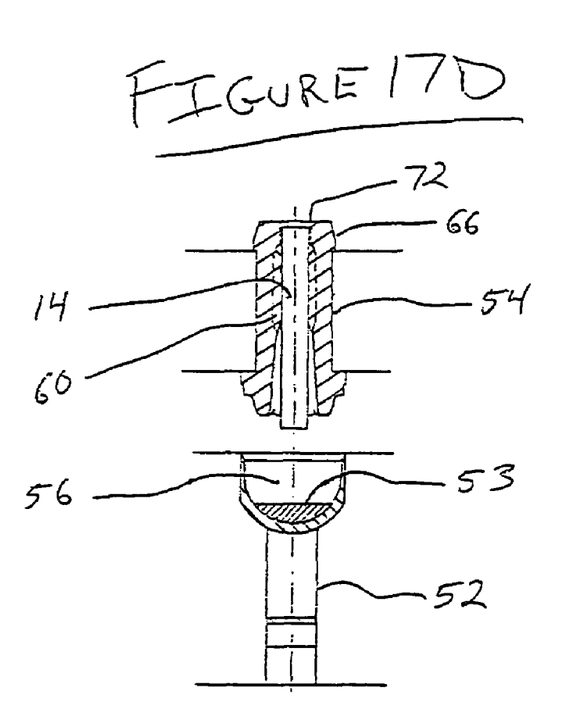

In FIGS. 17A and 17B, the component 14 is inserted into the cavity 58 of the mold upper portion 54 and retained therein by ribs 60. The foam 53 is disposed in the cavity 56 of the mold lower portion 52, as shown in FIG. 17C. The mold upper portion 54 with the component 14 inserted and retained therein is brought in proximity of the mold lower portion 52, as shown in FIG. 17D.

Figure 17E:
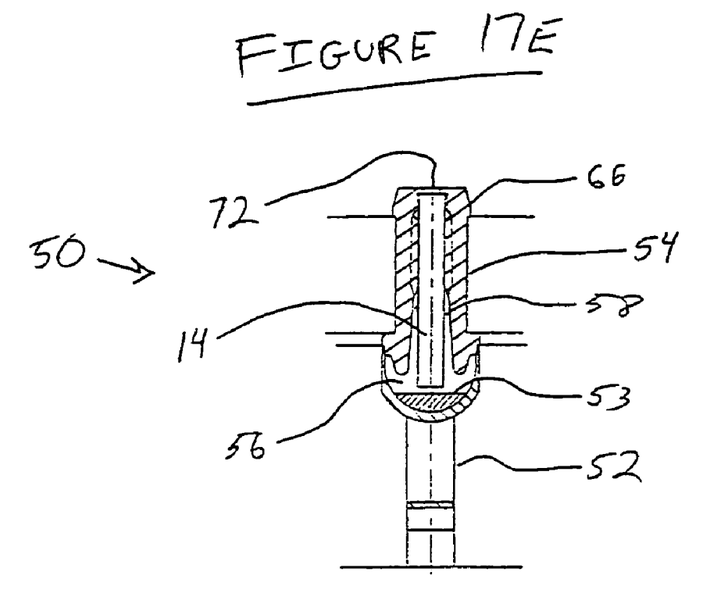
Figure 17F:
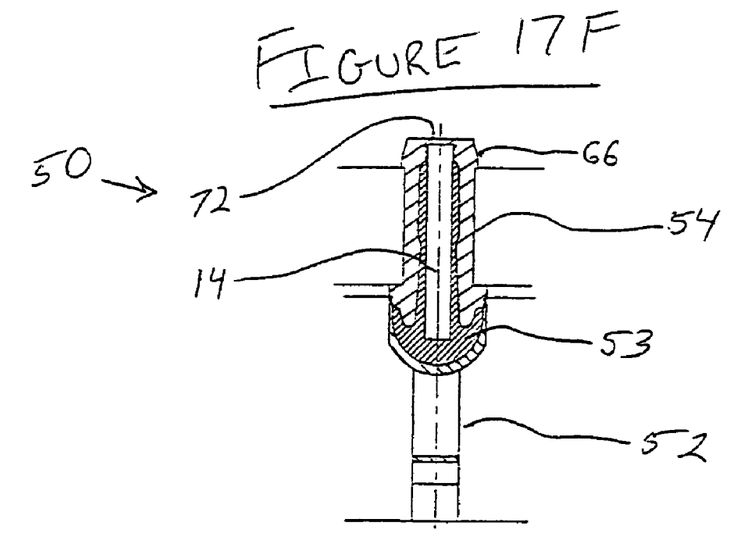

In FIGS. 17E and 17F, the cavities 56 and 58 are brought into communication, the component extending from the cavity 58 into the cavity 56. The foam 53 is then allowed and/or caused to rise throughout the cavities 56 and 58. In this way, a portion of the component 14 exposed to the cavities 56 and 58 is completely encapsulated by the foam 53. The foam 53 is then cured into a shape determined by the shape of the cavities 56, 58. During this process, the foam 53 forms a strong bond directly with the component 14.

During the foam rising process, gas within the mold cavities 56, 58 is permitted to pass through the vent passageways formed between the screw vent portion 72 and the component 14 when the gas attains a certain pressure within the cavities 56, 58. This gas, as mentioned, is air originally disposed within the cavities 56, 58 and/or any gas that may be evolved or otherwise present during the foaming process.

The screw threads 73 of the screw vent portion 72 prohibit the rising foam material from spilling to the exterior of the mold 50. However, a certain amount of the rising foam material 53 is permitted to enter the vent passageways and to cure therein, sealing off the cavities 56, 58 from the exterior of the mold 50, and thus maintaining a desired pressure therein for curing of the foam and formation of the earplug 10.

Figure 17G:
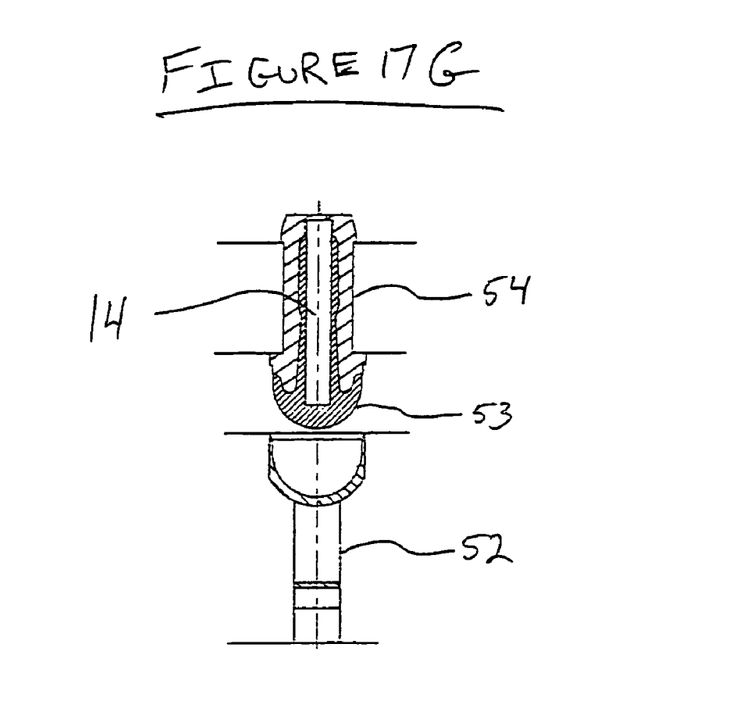

Once the foam 53 has cured, the mold upper portion 54 is removed from engagement with the mold lower portion 52, as shown in FIG. 17G. The component 14 remains retained in the mold upper portion by the ribs 60. The foam 53, now bonded with the component 14, leaves the cavity 56 of the mold lower portion 52.

Figure 17H:
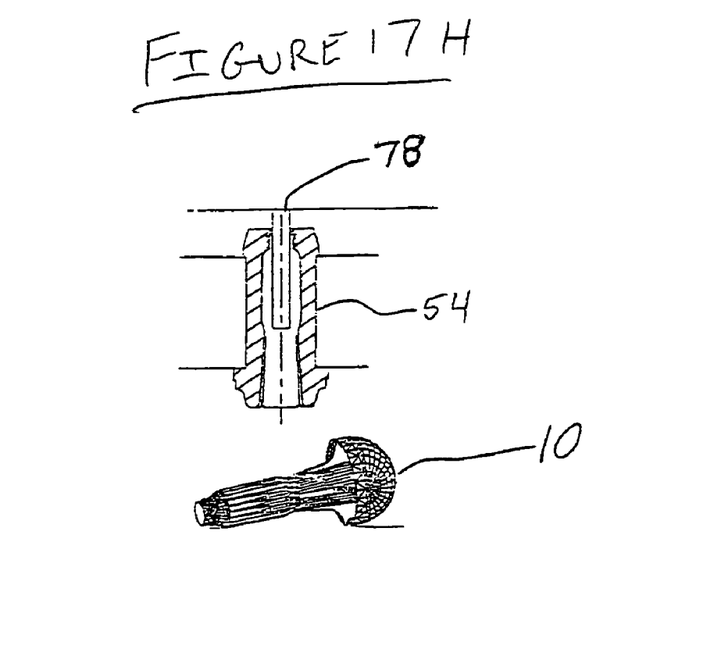

Then, as shown in FIG. 17H, a tool 78 is used to eject the component 14 with bonded foam 53 from the mold upper portion 54, thus completing the manufacturing of the earplug 10. Contact of the ribs 60 with the component 14 during manufacturing of the earplug 10 results in the formation of the depressions 22 which may be shaped as desired by shaping or contouring the ribs 60 accordingly.

The earplug 10 is also similarly manufactured utilizing the mold upper portion 54 having the knurled vent portion 74 and utilizing the mold upper portion 54 having the flange vent portion 76.

In another embodiment, continuous manufacture of a plurality of the earplugs 10 is provided by moving the mold lower portions 52 under a continuous pour machine which deposits a charge of the foam 53 in the cavities 53 and then engaging the mold upper portions with the mold lower portions to allow curing of the foam 53.

The invention, of which exemplary preferred embodiments are disclosed herein, provides a stemmed foam earplug that is effective in providing hearing protection, yet convenient and comfortable to use, and has a more efficient and lower cost method of manufacture. The earplug includes a foam insertion portion encapsulating and bonded directly to a component stem; the foam insertion portion providing a comfortable portion for an insertion into a wearer's ear; the component stem providing the necessary rigidity to facilitate proper insertion of the insertion portion into the ear and/or providing a means for connecting a cord, under the chin device, or headband component.

The method provided herein is particularly advantageous in that an effective earplug is produced easily, efficiently, at low cost, and without the necessity of an additional bonding step. Furthermore, the bond formed according to the present invention is strong and durable, resulting in a dependable earplug having a long use life.

The costs for manufacture of the invention are lower than for conventional earplugs because the disposing of the foam around the component eliminates the need for a separate bonding step, which was otherwise required to adhere the component to the foam and, further, because costly porous component stems are not required due to the disclosed venting means.

The venting means provided allows gas to escape from the cavities of the respective mold portions during the foaming process. The design of the venting means ensures that a desirable volume of gas escapes while preventing overflow of the foam from the cavities to the exterior of the mold. Further, the venting means allows a certain volume of the rising foam material to enter the vent passageways and to cure therein effectively sealing off the mold cavities from the exterior of the mold thus maintaining a desired pressure in the cavities optimal for curing the foam material and hence for forming the earplug.

The venting means allows utilization of simple, low cost component stems while ensuring consistent and optimal rising, curing, and bonding of the foam to form the earplug.

In these ways, the invention is effective for providing low cost, reliable hearing protection to a wearer which is convenient and comfortable to use.

While preferred embodiments have been shown and described, various modifications and substitutions may be made thereto without departing from the spirit and scope of the invention. Accordingly, it is to be understood that the present invention has been described by way of illustrations and not limitation.

The invention claimed is:

1. A mold for forming an earplug that has a foam insertable portion and a foam handle portion comprising:
   a lower mold portion including a lower cavity; and
   an upper mold portion including an upper cavity; the lower and upper cavity configured to form the ear plug having the foam insertable portion and the foam handle portion;
   a nestable component that is more rigid than the foam of the earplug, the nestable component being insertable into the upper cavity of the upper mold, such that the nestable component becomes secured to the foam handle portion and is bondable with the foam during a rising of the foam, and removable from the mold upon a bonding with the foam,
   wherein the upper cavity includes at least one projection defining a means for venting a gas during a rising of the foam;
   wherein the lower and upper mold portions are engageable so as to communicably engage the lower and upper cavities.

2. The mold of claim 1, wherein said means for venting comprises a screw thread helically disposed on the upper mold portion in the upper cavity.

3. The mold of claim 1, wherein said means for venting comprises a plurality of knurls disposed on the upper mold portion in the upper cavity.

4. The mold of claim 1, wherein said means for venting comprises at least one annular flange disposed on the upper mold portion in the upper cavity, the flange including at least one space formed therein to allow said venting of said gas.

5. A mold for forming an earplug that has a foam insertable portion and a foam handle portion comprising:
   a lower mold portion including a lower cavity;
   an upper mold portion including an upper cavity; the lower and upper cavity configured to form the ear plug having the foam insertable portion and the foam handle portion;
   a nestable component that is more rigid than the foam of the earplug, the nestable component being insertable into the upper cavity of the upper mold, such that the nestable component becomes secured to the foam handle portion and is bondable with the foam during a rising of the foam, and removable from the mold upon a bonding with the foam,
   wherein the upper cavity includes at least one projection defining a means for venting a gas during a rising of the foam; and
   a plurality of ribs projecting from the upper mold portion radially into the upper cavity and traversing the upper cavity in a longitudinal direction; wherein the lower and upper mold portions are engageable so as to communicably engage the lower and upper cavities.

6. The mold of claim 1, wherein when the lower and upper mold portions are engageable, the volume within remains essentially constant.

* * * * *

UNITED STATES PATENT AND TRADEMARK OFFICE
CERTIFICATE OF CORRECTION

PATENT NO. : 7,731,487 B2  Page 1 of 1
APPLICATION NO. : 11/357768
DATED : June 8, 2010
INVENTOR(S) : Richard E. Knauer

It is certified that error appears in the above-identified patent and that said Letters Patent is hereby corrected as shown below:

In the Specifications:

<u>Column 4</u>
Line 34, delete "wearerls" and insert -- wearer's -- therefore.

Signed and Sealed this

Twenty-sixth Day of October, 2010

David J. Kappos
*Director of the United States Patent and Trademark Office*